United States Patent [19]
Walz

[11] Patent Number: 5,760,093
[45] Date of Patent: Jun. 2, 1998

[54] HALOHYDROCARBON-FREE DELAYED RELEASE LACQUER SOLUTION FOR PHARMACEUTICAL PREPARATION

[75] Inventor: Michael Walz, Bingen/Rh., Germany

[73] Assignee: Boehringer Ingelheim KG, Ingelheim am Rhein, Germany

[21] Appl. No.: 236,931

[22] Filed: May 2, 1994

Related U.S. Application Data

[63] Continuation of Ser. No. 945,977, Nov. 6, 1992.

[51] Int. Cl.$^6$ ............... A61K 31/72; A61K 31/745
[52] U.S. Cl. ............... 514/772.4; 424/488; 424/494
[58] Field of Search ............... 514/772.4; 424/488, 424/494

[56] References Cited

U.S. PATENT DOCUMENTS 4,524,060  6/1985  Mughal et al. ............... 424/459
4,732,765  3/1988  Sasagawa et al. ............... 424/476

FOREIGN PATENT DOCUMENTS 2430766   6/1980  France.
60-169416 9/1985  Japan.
9215287   4/1992  WIPO.

OTHER PUBLICATIONS

Chem. Ab. 85: 51697 1976 Groshouyi et al.

Lippold et al Act. Pharmaceutica Tech. 27(3) 1981.

Primary Examiner—Thurman K. Page
Attorney, Agent, or Firm—Robert P. Raymond; Alan R. Stempel; Mary-Ellen Devlin

[57] ABSTRACT

The invention relates to a delayed-release lacquer solution for pharmaceutical preparations which is characterised in that it is free from halogenated hydrocarbons.

6 Claims, No Drawings

HALOHYDROCARBON-FREE DELAYED RELEASE LACQUER SOLUTION FOR PHARMACEUTICAL PREPARATION

This is a continuation of application Ser. No. 945,977, filed Nov. 6, 1992.

The invention relates to a delayed release lacquer solution for pharmaceutical preparations characterised in that it is free from halohydrocarbons.

With a view to controlling the release of active substances from solid pharmaceutical forms, distinctions are made between various mixtures and systems having different properties and release characteristics (matrix systems, coating systems, etc. A. N. Martin, J. Swarbrick, A. Cammarata; H. Stricker (Editor), Physikalische Pharmazie, 3rd Edition, Stuttgart: Wissenschaftliche Verlagsgesellschaft, 1987).

For the purpose of achieving a constant release of active substances the principle of coating blanks which contain active substances with a semi-permeable diffusion coating has become more and more prevalent. Such coatings often consist of an insoluble component such as ethylcellulose and a soluble component such as polyethyleneglycol incorporated therein. A typical recipe for delayed-release coatings of this kind consists, for example, of ethylcellulose and polyethyleneglycol as solids and ethanol and dichloromethane as solvents. Halohydrocarbons, particularly dichloromethane, are characterised by their exceptional dissolving capacity for numerous pharmaceutical adjuvants and have hitherto freely been used as solvents for preparing such coatings for pharmaceutical preparations such as tablets, pellets and granules.

However, the use of halogenated hydrocarbons is now in doubt for reasons of environmental protection and for toxicological reasons, with a result that it is desirable to refrain from using these substances.

However, it is not possible simply to replace the halogen-containing delayed-release lacquer solutions by aqueous dispersion systems, which have been on the market for some time. The film coatings obtained from these systems generally have completely different release characteristics. Furthermore, there are frequently problems with the constancy of the release characteristics or stability problems caused by interactions between the active substance and the excipients which are required technologically in these preparations. The use of halogen-free organic solvent systems has hitherto frequently failed because of the poor dissolving properties of the alternative solvents for the lacquer components such as ethylcellulose and polyethyleneglycol and particularly because of the different release characteristics of film coatings consisting of delayed-release lacquer systems of this kind. The structure of the lacquer coating and hence its release characteristics are determined, once again, by the solvent used.

Thus, in early experiments with different solvent mixtures, there was either an inadequate delaying effect or the release of the active substance was excessively delayed. Many solvent systems were unusable owing to their poor dissolving properties for the film forming agents.

Surprisingly, it has been found that when specific solvent systems are used having a precisely defined, relatively low water content, it is possible to prepare delayed-release lacquer solutions which are easy to process, which yield diffusion coatings having release characteristics comparable with those achieved with delayed-release lacquer solutions which contain halohydrocarbons.

According to the invention, a two-component lacquer solution is proposed which contains a water-insoluble film forming agent and a water-soluble polymer, the solvent system used being a low-boiling alcohol having a defined water content of between 0.5 and 15% by weight or a mixture of a low boiling alcohol and a low boiling ketone, the water content being between 0.5 and 10% by weight.

The delayed-release lacquer solution according to the invention is intended for the production of diffusion coatings for controlling the release of pharmaceutically active substances, by spraying (under suitable conditions) onto blanks (pressed tablets, pellets and other pharmaceutical blanks).

The suitable conditions referred to relate inter alia to the dissolving and expansion properties of the blanks technical factors of the coating apparatus (the type of apparatus, its size, nozzle, spraying distance etc.)

the climatic conditions during spraying the procedure adopted during spraying (spraying speed, method of drying, etc.).

The conditions correspond substantially to those of the known solutions which contain halohydrocarbons and are known to those skilled in the art.

The blanks coated in this way have comparable qualities, particularly in terms of the release of active substance, to the blanks coated with conventional lacquer solutions which contain halogen/dichloromethane.

According to the invention, pharmaceutical-grade ethylcellulose is used as the water-insoluble film forming agent, eg. ethylcellulose having an ethoxyl content of about 45–50%, preferably about 48–49.5% (eg. Hercules Type N) and with a viscosity (5% solution in toluene/ethanol 80:20) of 8–24 cps, preferably 12–16 cps (eg. Type N 14 made by Hercules); polyethyleneglycol is used as the water-soluble polymer. The molecular weight can be between 1000 and 10000, preferably between 4000 and 8000 (eg. polyethyleneglycol Type 6000 made by Hoechst).

The concentration of solids in the solvent is 2–15% by weight, preferably 5–10% by weight. Of the solid material, the proportion of ethylcellulose is 20–80% by weight, preferably 50–70% by weight and the proportion of polyethyleneglycol is 20–80% by weight, preferably 30–50% by weight.

Examples of suitable solvents include low boiling alcohols such as methanol, ethanol, propanol, isopropanol, 1-butanol and 2-butanol, ethanol and isopropanol being preferred.

The amount of water added is 0.5–15%, preferably 4–10%, based on the anhydrous alcohol.

Mixtures of low boiling alcohols and ketones, preferably ethanol/acetone or isopropanol/acetone, are also suitable. Another suitable ketone is methylethyl ketone.

The ratio of alcohol to ketone may vary within a ratio from 10:90 to 90:10, preferably 40:60 to 60:40, the amount of water added being between 0.5 and 10%, preferably from 1–5%.

A preferred delayed-release lacquer solution according to the invention contains ethanol with 4–10% water or ethanol/acetone 1:1 with 1–5% water as solvent, 5–10% solids consisting of 50–70% ethylcellulose and 30–50% polyethyleneglycol.

The Examples which follow are intended to illustrate the invention without restricting it to the examples given.

EXAMPLE 1

| Example 1 | |
|---|---|
| Tablets | |
| Parameters | |
| Active substance | Bunitrolol |
| Form | round, convex, radius of curvature 5.5 mm |
| Dimensions | diameter 5 mm, thickness about 2.5 mm |
| Mass | 50 mg |
| Coating constituents | |

| Name | Ethylcellulose | Polyethyleneglycol |
|---|---|---|
| Type | N 14 | 6000 |
| Manufacturer | Hercules | Hoechst |
| Solids content | 60% | 40% |
| Solvent | | |

| Title | Actone | Ethanol | Water |
|---|---|---|---|
| Quality | technical goods | Absolute ethanol denatured with methylethylketone | purified water |
| Composition solvent system | 49.5% | 49.5% | 1% |

Delayed-Release Lacquer Solutions

Parameters

| | |
|---|---|
| Solids concentration | 10% |
| Method of production | weighing the solvent mixture dissolving polyethyleneglycol 6000 (with heating to about 40° C.) stirring in ethylcellulose N 14 (after cooling to below 30° C.) mixing the solution |

Film Spraying

Parameters

| | |
|---|---|
| Batch size Tablets | 10 kg = about 200,000 tablets |
| Quantity of lacquer per tablet | 6 mg |
| Coating apparatus | Accela-Cota 24 (made by Manesty, of Liverpool) |
| Spray gun | Walther Pilot WA XV nozzle: 1.3 mm |
| Spraying air over pressure | 1.5 bar |
| Air fed in | about 51° C. |
| Air discharged | about 31° C. |
| Temperature of substance | about 32° C. |

Drying of Film-Coated Tablets

Parameters

| | |
|---|---|
| Drying apparatus | Accela-Cota |
| Air fed in | 40° C. |

| Example 2 | |
|---|---|
| Tablets | |
| Parameters | |
| Active substance | Bunitrolol |
| Form | round convex, radius of curvature 5.5 mm |
| Dimensions | diameter 5 mm, thickness about 2.5 mm |
| Mass | 50 mg |
| Coating constituents | |

| Name | Ethylcellulose | Polyethyleneglycol |
|---|---|---|
| Type | N 14 | 6000 |
| Manufacturer | Hercules | Hoechst |
| Solids content | 60% | 40% |
| Solvent | | |

| Title | Actone | Ethanol | Water |
|---|---|---|---|
| Quality | technical goods | Absolute ethanol denatured with methylethylketone | purified water |
| Composition solvent system Solvent system | — | 96% | 4% |

Manufacture continues as described in Example 1.

What is claimed is:

1. A delayed-release, halohydrocarbon-free lacquer solution for pharmaceutical preparations containing ethylcellulose, polyethylene glycol and as solvent, one or more low boiling point alcohols and ketones, characterised in that the solvent has water added thereto in an amount from 0.5–10% by weight and that the solids content of the solution contains about 20–80% by weight ethylcellulose having an ethoxyl content of about 45–50% and about 20–80% by weight polyethylene glycol with a molecular weight between 4,000 and 10,000.

2. The delayed-release, halohydrocarbon-free lacquer solution according to claim 1, characterised in that the solids content of the solution is from 2–15% by weight.

3. The delayed release, halohydrocarbon-free lacquer solution according to claim 2, characterised in that the solids contain 20–80% by weight ethylcellulose and 20–80% by weight polyethylene glycol.

4. The delayed release, halohydrocarbon-free lacquer solution according to claim 1, characterised in that the solvent is anhydrous ethanol, isopropanol containing 4–10% by weight added water or a mixture of anhydrous ethanol/acetone or isopropanol/acetone in the ratio of 1:1 with added water in an amount from 1–5% by weight.

5. A method of using the delayed-release halohydrocarbon-free lacquer solution according to any one of claims 1, 2, 3, 4 or 6 for the preparation of diffusion coatings on pharmaceutical preparations for controlling release of pharmaceutically active substances comprising the step of coating blanks which contain active substances with the solution.

6. The delayed-release halohydrocarbon-free lacquer solution according to claim 3, characterised in that the solids contain 50–70% by weight ethylcellulose and 30–50% by weight polyethylene glycol.

* * * * *